United States Patent
Munaka et al.

(10) Patent No.: US 9,279,802 B2
(45) Date of Patent: Mar. 8, 2016

(54) CELL SORTER AND CELL SORTING METHOD

(75) Inventors: Tatsuya Munaka, Kyoto (JP); Hirohisa Abe, Kyoto (JP); Masaki Kanai, Nara (JP); Taira Maekawa, Kyoto (JP); Shinya Kimura, Kyoto (JP); Eishi Ashihara, Kyoto (JP)

(73) Assignees: SHIMADZU CORPORATION, Kyoto (JP); KYOTO UNIVERSITY, Kyoto (JP)

( * ) Notice: Subject to any disclaimer, the term of this patent is extended or adjusted under 35 U.S.C. 154(b) by 200 days.

(21) Appl. No.: 14/342,583

(22) PCT Filed: Aug. 16, 2012

(86) PCT No.: PCT/JP2012/070788
§ 371 (c)(1),
(2), (4) Date: Mar. 4, 2014

(87) PCT Pub. No.: WO2013/046980
PCT Pub. Date: Apr. 4, 2013

(65) Prior Publication Data
US 2014/0227733 A1    Aug. 14, 2014

(30) Foreign Application Priority Data
Sep. 27, 2011 (JP) .................. 2011-210160

(51) Int. Cl.
*C12M 3/00* (2006.01)
*G01N 33/50* (2006.01)
*C12Q 1/28* (2006.01)
*C12M 1/00* (2006.01)

(52) U.S. Cl.
CPC .......... *G01N 33/5029* (2013.01); *C12M 47/04* (2013.01); *C12Q 1/28* (2013.01)

(58) Field of Classification Search
None
See application file for complete search history.

(56) References Cited

U.S. PATENT DOCUMENTS

| 5,861,306 A | 1/1999 | Pugh et al. |
| 5,874,266 A | 2/1999 | Palsson |
| 2011/0033910 A1 | 2/2011 | Yamanaka et al. |
| 2013/0164848 A1 | 6/2013 | Munaka et al. |

FOREIGN PATENT DOCUMENTS

| JP | 6-327494 A | 11/1994 |
| JP | 9-56369 A | 3/1997 |
| JP | 2002-511843 A | 4/2002 |
| WO | 2009/128483 A1 | 10/2009 |
| WO | 2012/032844 A1 | 3/2012 |

OTHER PUBLICATIONS

C. Lo Celso et al., "Live-animal tracking of individual haematopoietic stem/progenitor cells in their niche", Nature vol. 457, Jan. 2009, pp. 92-96, cited in the Specification.
Weilbaecher et al., "Cancer to bone: a fatal attraction", Nature Reviews Cancer vol. 11, pp. 411-425, Jun. 2011, cited in the Specification.
Mohamed Gad-El-Hak ed., "The MEMS Handbook", second edition, pp. 10-6-10-7 (2009), cited in the Specification.
Fu et al., "An Integrated Microfabricated Cell Sorter", Analytical Chemistry, Jun. 1, 2002, vol. 74, No. 11, p. 2451-2457.
International Search Report, dated Nov. 13, 2012, issued in corresponding application No. PCT/JP2012/070788.

*Primary Examiner* — Ralph Gitomer
*Assistant Examiner* — Trent Clarke
(74) *Attorney, Agent, or Firm* — Westerman, Hattori, Daniels & Adrian, LLP

(57) ABSTRACT

A cell sorter including a well that has a microspace filled with a liquid and having a typical length of 1 mm or less, and that has a bottom surface made of a light-permeable material allowing optical observation of an interior of the microspace; a matrix provided on the bottom surface in the well; a bone fragment placed on the matrix in the well; and osteoclasts placed between the matrix and the bone fragment.

6 Claims, 4 Drawing Sheets

Without Osteoclasts (A) At Start of Observation

Bone Fragment 50.0 μm (B) After Lapse of 4.5 hours

Bone Fragment 50.0 μm

CELL SORTER AND CELL SORTING METHOD

TECHNICAL FIELD

The present invention relates to a cell sorter for use in sorting out cancer stem cells from other cells and a cell sorting method using the cell sorter.

BACKGROUND ART

In recent years, in vivo microenvironments have attracted attention. Among them, a system in which osteoclasts are present in a bone-marrow microenvironment is considered not only to be the front line of bone remodeling that is the original function of the system but also to provide a niche comfortable for other cells. Further, it is considered that cancer stem cells, which have drug resistance and interfere with the radical cure of cancer, are deeply involved with the presence of the niche.

It is considered that cancer stem cells are sources of many cancer cells and have drug resistance, and therefore, interfere with the eradication of cancer. Thus, drug discovery targeting cancer stem cells is considered to be important for the radical cure of cancer. In order to investigate the effect of a drug targeting cancer stem cells, it is necessary to sort out cancer stem cells from other cells. However, a method for sorting out cancer stem cells from other cells has not hitherto been established.

PRIOR ART DOCUMENTS

Non-Patent Documents

Non-Patent Document 1: C. Lo Celso, H. E. Fleming, J. W. Wu, C. X. Zhao, S. Miake-Lye, J. Fujisaki, D. Cote, D. W. Rowe, C. P. Lin, D. T. Scadden, Live-animal tracking of individual haematopoietic stem/progenitor cells in their niche, Nature 457 (2008) 92-96.

Non-Patent Document 2: Weilbaecher, K. N., Guise, T. A. & McCauley, L. K. Cancer to bone: a fatal attraction. Nature Reviews Cancer 11,411-425 (2011).

Non-Patent Document 3: Mohamed Gad-el-Hak, The MEMS HANDBOOK, second edition, pp. 10-6-pp. 10-7 (2009)

SUMMARY OF THE INVENTION

Problems to be Solved by the Invention

Cell functions include, for example, cell characteristics such as cell migration and invasion as well as characteristics such as surface antigen, cell cycle, and drug resistance. These functions can be generally evaluated by optical observation. However, cancer stem cells are considered to interact with a microenvironment (niche) around them to express their functions. Therefore, the direct observation of such an interaction is considered as a simple and effective method for investigating the influence of a bone-marrow microenvironment on cancer stem cells. However, the direct observation of the interaction between cancer stem cells and a bone-marrow microenvironment involves the following two problems.

The first problem is the influence of convection. A bone-marrow microenvironment has a size of several micrometers to several hundred micrometers, and is therefore less likely to be influenced by flow or mixing so that convection hardly occurs. This environment has a special characteristic that migration of humoral factors is controlled by diffusion. However, vessels generally used in conventional cell culture, such as petri dishes, flasks, or well plates, have a large capacity, and heat sources such as a carbon dioxide incubator, a microscope illumination lamp, a fluorescent lamp, and other electric devices are present, and therefore, liquid migration mainly caused by heat convection occurs in these vessels. Therefore, it cannot be said that the environment in these vessels is an accurate reproduction of a bone-marrow microenvironment.

The second problem is the difficulty of real-time observation. Most conventional observation methods use a combination of photographs of tissue sections at some point in time. Non-Patent Document 1 discloses an example of real-time observation using very thin sections. However, in this example, a sample is exposed to the atmosphere, and therefore, the conditions of an original bone-marrow microenvironment, such as an oxygen concentration gradient, are changed. For this reason, it is unlikely that information about the activities of cells in a living body can be accurately obtained.

It is therefore an object of the present invention to make it possible to directly observe the characteristics of cells in a bone-marrow microenvironment and to perform cell sorting based on the observation results.

Solutions to the Problems

The present invention is directed to a cell sorter including: a well that has a microspace filled with a liquid and having a typical length of 1 mm or less and has a bottom surface made of a light-permeable material allowing optical observation of an interior of the microspace; a matrix provided on the bottom surface in the well; a bone fragment placed on the matrix in the well; and osteoclasts placed between the matrix and the bone fragment. Here, "typical length" means a characteristic length for use in calculating Reynolds number in fluid mechanics. For example, in the case of a rectangular flow channel, the typical length is generally 4×(cross-sectional area/perimeter of cross section), and in the case of a circular tube, the typical length is generally D (diameter) (see Non-Patent Document 3). Further, the "matrix" means "bone matrix" that is an extracellular component constituting bone, and refers to, for example, collagen fibers or hydroxyapatite. The main constituent protein of bone matrix is type I collagen, and other constituent proteins of bone matrix are osteocalcin, osteopontin, bone morphogenetic proteins, and the like. Hereinafter, the "bone matrix" is simply referred to as "matrix".

The present invention is also directed to a cell sorting method using the cell sorter according to the present invention. Sample cells labeled with a phosphor are placed around the bone fragment in the well of the cell sorter according to the present invention, and the positions of the sample cells are optically observed after a lapse of a certain period of time to sort out the cells that migrate into a space between the matrix on the bottom surface of the well and the bone fragment from the cells that do not migrate.

The present inventors have found that when sample cells are placed around a bone fragment to which osteoclasts are attached, some of the cells migrate so as to be attracted to a portion to which osteoclasts are attached. The cell sorting method according to the present invention is based on this finding.

In an experiment by the present inventors, cell migration was observed when osteoclasts were attached to a bone fragment, but was not observed when osteoclasts were not attached to a bone fragment. From this, it is considered that a substance released from bone or osteoclasts by bone resorption by osteoclasts attracts cells. According to Non-Patent Document 2, calcium ($Ca^{2+}$), various cytokines (TFG-$\beta$), and growth factors (IGFs) are released by bone resorption by osteoclasts. Therefore, it is considered that any of these substances serves as an attractant that allows certain cells to migrate.

Effects of the Invention

In the cell sorter according to the present invention, a microspace having a typical length of 1 mm or less is provided in a well to prevent the occurrence of convection in a solution filling the well, and a matrix is provided on a bottom surface of the microspace, and a bone fragment is placed on the matrix to reproduce a bone-marrow microspace. Further, the bottom surface of the well is made of a light-permeable material that allows the optical observation of an interior of the microspace, which makes it possible to optically observe the characteristics of cells in the microspace as a reproduction of a bone-marrow microspace from the bottom surface side in real time. Further, the microspace is in a state where osteoclasts get in between the matrix and the bone fragment, and therefore, substances such as calcium and cytokines are released by bone resorption by the osteoclasts, which makes it possible to sort out cells that are attracted by these substances and migrate from cells that do not migrate.

The cell sorting method according to the present invention using the cell sorter described above makes it possible to easily and optically observe the behavior of sample cells in real time by previously labeling the sample cells with a phosphor.

BRIEF DESCRIPTION OF THE DRAWINGS

FIG. 3 shows the GFP fluorescence microscopy images of the interior of the well of the cell sorter, in which osteoclasts were guided under the bone fragment, wherein FIG. 3(A) is the image obtained at the start of observation and FIG. 3(B) is the image obtained after a lapse of 4.5 hours.

FIG. 4 shows the GFP fluorescence microscopy images of the interior of the well of the cell sorter, in which osteoclasts were not guided under the bone fragment, wherein FIG. 4(A) is the image obtained at the start of observation and FIG. 4(B) is the image obtained after a lapse of 4.5 hours.

EMBODIMENTS OF THE INVENTION

In a preferred embodiment of a cell sorter according to the present invention, a collagen gel obtained by mixing acid-soluble Type-I collagen derived from porcine tendon developed for tissue culture, a concentrated medium, and a reconstitution buffer is used as a matrix, and a bottom surface of a well is coated with the collagen gel to reproduce a bone-marrow microenvironment.

It is to be noted that as the matrix, a gel prepared from a soluble basement membrane extracted from Engelbreth-Holm-Swarm (EHS) mouse sarcoma rich in extracellular matrix proteins or hydroxyapatite may be used instead of the collagen gel.

When the well is a cylindrical well, the typical length of the well may be its diameter. In this case, the depth of the well is preferably 300 µm or less. This makes it possible to prevent the occurrence of convection in a solution to reproduce an environment close to a bone-marrow microenvironment in the interior space of the well.

Further, the concentration of oxygen in a position where osteoclasts are placed is preferably about 5%. This makes it possible to create an environment close to a bone-marrow microenvironment in an area where osteoclasts are placed because the concentration of oxygen in a bone-marrow microenvironment is considered to be about 5%.

A cell sorting method according to the present invention may use, for example, green fluorescent protein as a fluorescent agent for labeling sample cells.

Figure 1:
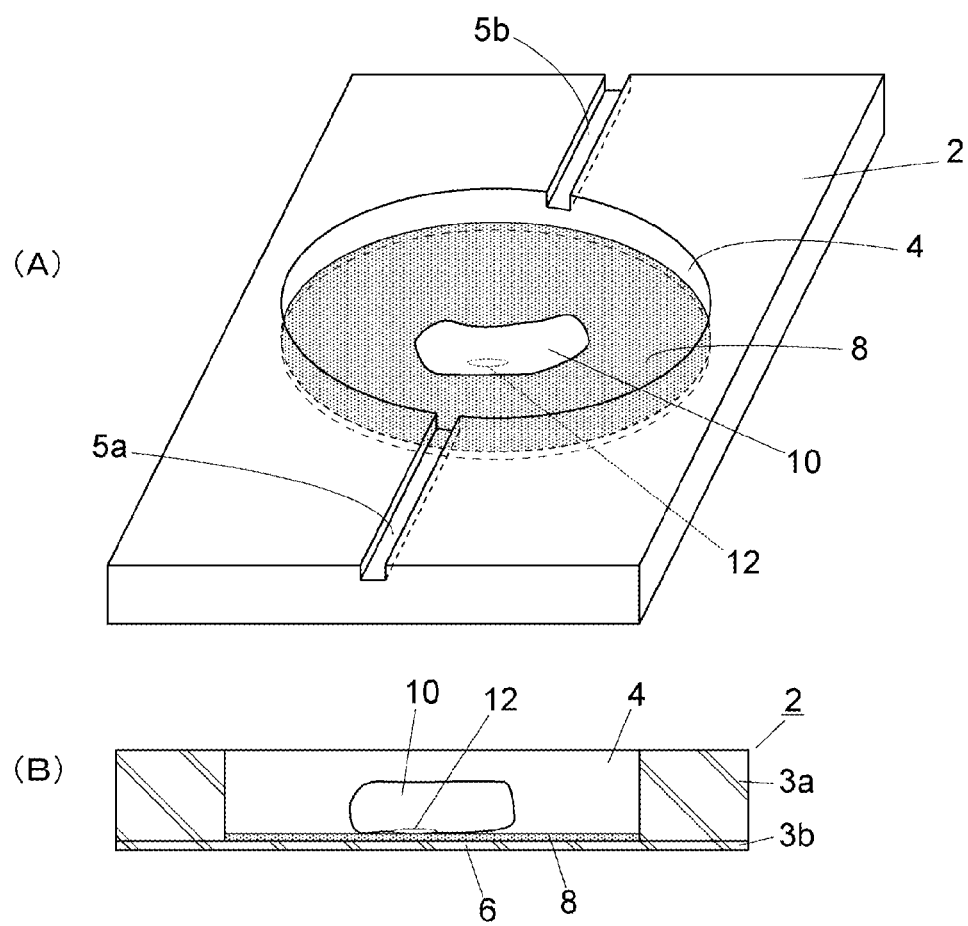
FIG. 1(A) is a perspective view of one example of a cell sorter and FIG. 1(B) is a sectional view showing the interior of a well.

One example of the cell sorter will be described with reference to FIG. 1.

The cell sorter is constructed as a chip 2. The chip 2 is made of a material such as PDMS (polydimethylsiloxane), quartz glass, or silicon, and is constituted from a first substrate 3a having a through hole as a well 4 and a second substrate 3b bonded to one of the surfaces of the first substrate 3a. The well 4 is formed using a microfabrication technique called µTAS (micro Total Analysis system) or microfluidics. The interior space of the well 4 is a microspace having a typical length of 1 mm or less.

In this example, the well 4 has a circular bottom surface, a diameter of 1 mm as a typical length, and a depth of 300 µm. The bottom surface 6 of the well 4 has a thickness of 0.17 mm and is configured so that the interior of the well 4 can be optically observed from the bottom surface 6 side. The chip 2 has grooves 5a and 5b formed on the upper surface side thereof as flow channels for introducing and discharging a solution into and from the well 4. Although not shown in FIG. 1, the upper surface side of the chip 2 is covered with a member such as a PDMS substrate to seal the upper surface of the well 4, at which time the grooves 5a and 5b form flow channels.

On the bottom surface of the well 4, a collagen gel coating is provided as a matrix 8. On the matrix 8, a bone fragment 10 is placed. When the bone fragment 10 has, for example, a rectangular parallelepiped shape, its size is about 200 µm, which is the same scale as a bone-marrow microenvironment. Between the matrix 8 and the bone fragment 10, osteoclasts 12 are placed. The osteoclasts 12 are differentiated from osteoblasts. The chip 2 shown in FIG. 1 is in a state where its upper surface is opened. However, when the chip 2 is used, the well 4 is filled with, for example, a cell suspension that is a mixture of many cells to be subjected to sorting and a medium (a) and/or a liquid (b) such as water or a buffer solution typified by phosphate buffered saline, and the upper surface of the well 4 is sealed with a sealing member made of, for example, PDMS. Here, the many cells are cells as an object to be subjected to sorting by the present invention, and refer to two or more cells that can be suspended under normal experimental conditions, but the present invention is effective also for a single cell, and therefore, the object to be subjected to sorting by the present invention includes a single cell.

The capacity of the well 4 is about 240 nL and very small. Therefore the apparent viscosity of a solution filling the well 4 increases, which makes it possible to perform an experiment without being influenced by convection or stirring. Rayleigh number Ra that is a dimensionless number that characterizes heat transfer by natural convection can be used to determine whether or not convection occurs in the solution in the well. Rayleigh number Ra is represented by the following formula.

$$Ra = (L^3 \cdot g \cdot \beta \cdot \Delta T)/\upsilon a$$

It is to be noted that L is the typical length of the well 4, g is the acceleration of gravity, β is the coefficient of thermal expansion of fluid, υ is kinematic viscosity, a is thermal conductivity, and ΔT is typical temperature difference.

Transition from laminar to turbulent flow in natural convection or formation of Benard cells (which are a kind of convective structure and refer to regularly-divided cell-like structures formed by uniformly heating a thin fluid layer from the bottom surface thereof) by convection is defined by the value of Rayleigh number Ra. Critical Rayleigh number Ra' at which Benard cells start to be formed in a horizontal fluid layer is 1708, wherein the thickness of the fluid layer is defined as L, the temperature difference between the upper and lower surfaces of the fluid layer is defined as ΔT, and the upper and lower surfaces are solid surfaces. It is to be noted that g=9.8 m/s$^2$, β=0.2×10$^{-3}$/° C., υ=1×10$^{-2}$ cm$^2$/s, and a=1.41×10$^{-3}$ cm$^2$/s.

For example, when the typical length L is 10 cm, Rayleigh number Ra is calculated as follows:

$$Ra = 10^3 \times 980 \times 0.2 \times 10^{-3} \times \Delta T / (1 \times 10^2 \times 1.41 \times 10^{-3})$$
$$= 980 \times 0.2 / 1.41 \times \Delta T \times 10^2 \times 10^3$$
$$= 139 \times 10^5 \times \Delta T$$
$$\approx 1.4 \times 10^7 \times \Delta T.$$

The typical temperature difference ΔT' at the time when Ra=Ra' (=1708) is as follows:

ΔT'=1.2×10$^{-4}$ (° C.). That is, it is considered that convection occurs in the solution in the well when the typical temperature difference is 1.2×10$^{-4}$° C. or larger.

On the other hand, when the typical length L of the well is 1 mm, Ra is as follows:

$$Ra = 10^3 \times 980 \times 0.2 \times 10^{-3} \times \Delta T / (1 \times 10^2 \times 1.41 \times 10^{-3})$$
$$= 14 \times \Delta T.$$

The typical temperature difference ΔT' at the time when Ra=Ra' (=1708) is as follows:

ΔT'=120 (° C.). That is, it is considered that convection does not occur in the solution in the well until the typical temperature difference reaches 120° C. or larger.

The temperature in the well 4 is 37° C., and thus, the actual typical temperature difference between the temperature in the well 4 and room temperature (25° C.) is about 12° C. at most. Therefore, it cannot be considered that the typical temperature difference becomes larger than the above ΔT' (120° C.). From this, it is considered that natural convection does not occur in the solution in the well 4 by setting the typical length of the well 4 to 1 mm or less.

One example of a method for producing the cell sorter of this example will be described.

This cell sorter is constructed as a system in which specific cancer cells migrate in a bone-marrow microenvironment reconstructed in the well 4 of the chip 2 by co-culturing bone, osteoblasts, and bone-marrow cells so that the osteoclasts 12 are guided between the bone fragment 10 and the matrix 8.

The chip 2 uses a silicon substrate having a thickness of 300 μm as the first substrate 3a. The silicon substrate 3a is etched using a microfabrication technique to form a circular through hole having a diameter of 1 mm. A transparent glass substrate having a thickness of 0.17 mm as the second substrate 3b is anodically-bonded to one of the surfaces of the silicon substrate 3a to form the bottom surface 6 of the well 4.

Next, the surface of the glass substrate 3b as the bottom surface 6 in the well 4 is coated with a collagen gel to form the matrix 8. Then, the bone fragment 10 having a size of about 200 μm is placed on the matrix 8. The size of the bone fragment 10 is not particularly limited as long as the bone fragment 10 can be accommodated in the well 4. When the bone fragment 10 has, for example, a rectangular parallelepiped shape, its maximum dimension is about 200 μm.

Figure 2:
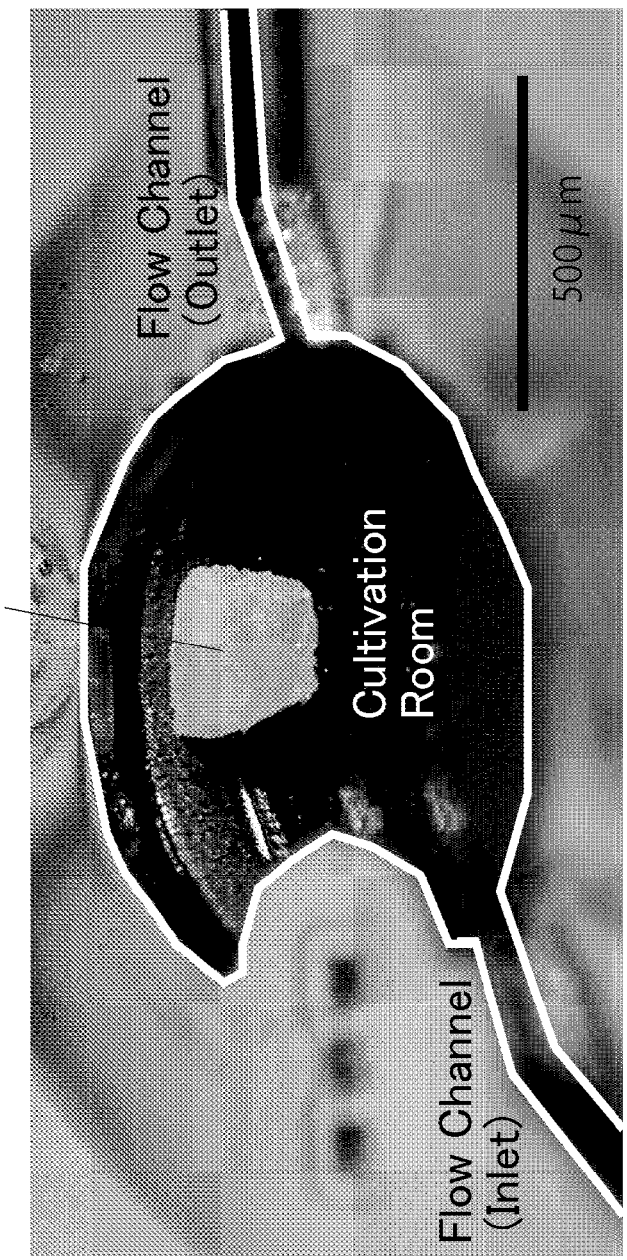
FIG. 2 is an image showing a state where a bone fragment is placed in the well of the cell sorter.

FIG. 2 is an image showing a state where the bone fragment 10 is actually placed in the well 4. The bone fragment 10 is prepared by removing a femur from a 5- to 10-week old BALB/cA mouse, flushing out (washing) bone marrow with a medium, and cutting the femur with a surgical knife. After a medium is charged into the well 4, the upper surface of the well 4 is sealed with a member formed from, for example, a PDMS substrate so that a medium or a cell suspension in the well 4 is not exposed to the atmosphere except during operation such as supply of various cells or a medium into the well 4 or medium replacement. It is to be noted that the capacity of the interior of the well 4 (cultivation room) of the chip 2 is 240 nL.

Osteoblasts obtained from the parietal bone of a 1- to 2-day-old BALB/cA mouse are introduced into the well 4 in a concentration of about 200 cells/well. After the osteoblasts are adhered to the bottom surface of the well 4 in 4 to 6 hours, bone marrow cells obtained by flushing out the bone marrow of the femur of the 5- to 10-week-old BALB/cA mouse are introduced in a concentration of about 800 cells/well. To the well 4, α MEM containing 10% bovine fetal serum, 0.02 μM vitamin D3, and 2 μM prostaglandin E2 are added as a medium to perform co-culture under water vapor-saturated conditions at 37° C. and 5% $CO_2$. The co-culture is performed for 7 to 10 days while the medium is replaced several times to differentiate the bone-marrow cells into osteoclasts. The osteoclasts get under the bone fragment 10. FIG. 1 shows this situation. It is to be noted that in FIG. 1, the osteoblasts and the bone-marrow cells are not shown.

One example of cell sorting performed using the cell sorter of this example will be described.

As sample cells, leukemic cell line cells labeled with green fluorescent protein (GFP) (Ba/F3 wt bcr-abl GFP) were introduced into the well 4 at a density of about 100 cells/well. The upper surface of the well 4 was sealed with a PDMS substrate, and then so-called time-lapse observation was immediately performed using a fluorescence microscope to take GFP fluorescence images at regular time intervals through the bottom surface 6 of the well 4 from the back surface side of the chip 2 (from the bottom surface 6 side of the well 4). The chip 2 was placed on a stage in a temperature and $CO_2$ control chamber with mixing device set in the fluorescence microscope. The stage was maintained in a water vapor-saturated environment at 37° C. and 5% $Co_2$. After the completion of the time-lapse observation of the chip, TRAP (Tartrate-Resistant Acid Phosphatase) staining was performed to identify the positions of osteoclasts.

Figure 3:
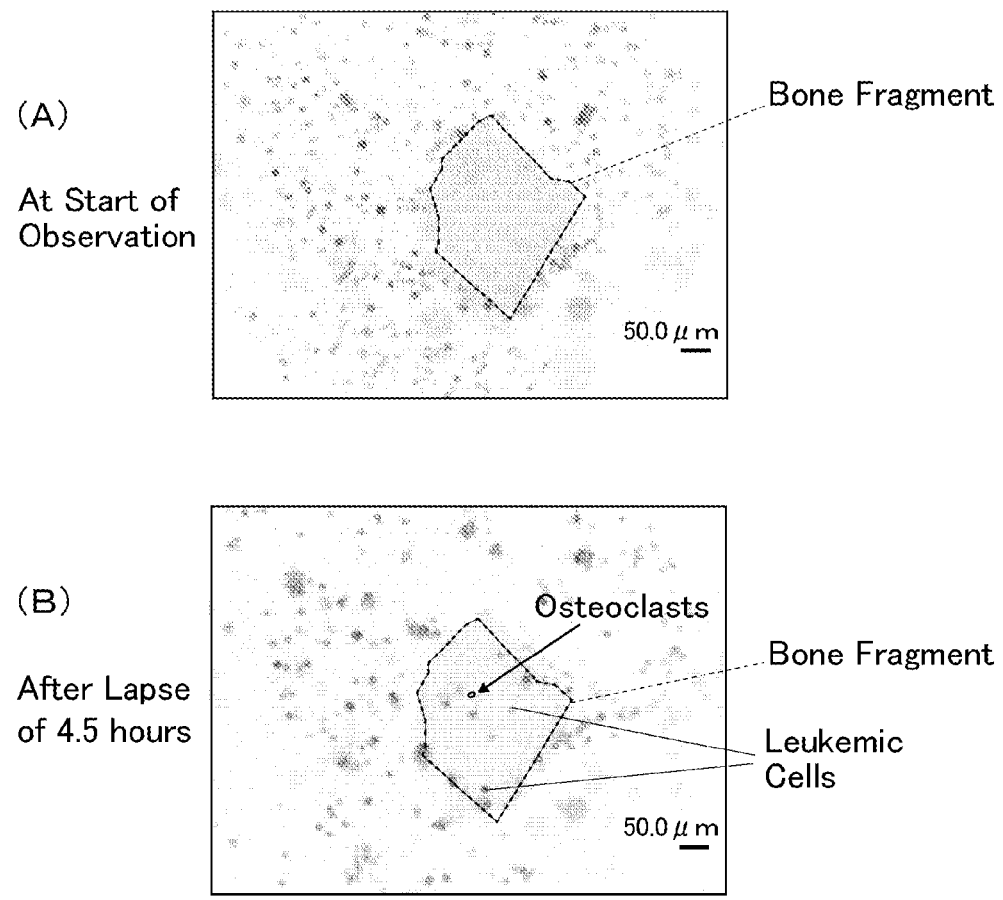

FIG. 3 shows the GFP fluorescence microscopy images of the interior of the well 4 of the cell sorter in which osteoclasts were guided under the bone fragment.

At the start of the observation, as shown in FIG. 3(A), the leukemic cells were not present under the bone fragment, but were distributed almost evenly in other places. After about two hours, some of the leukemic cells started to get under the bone. Then, after a lapse of 4.5 hours, as shown in FIG. 3(B), some of the leukemic cells stayed under the bone fragment.

Figure 4:
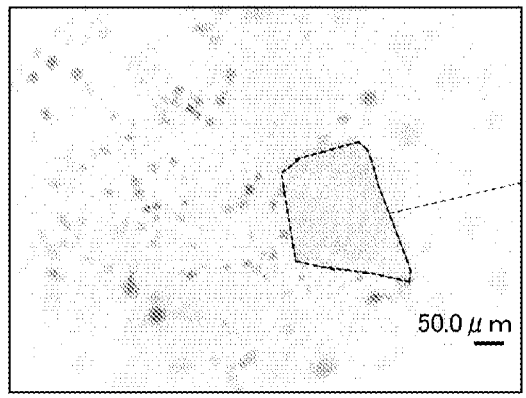
Figure 4:
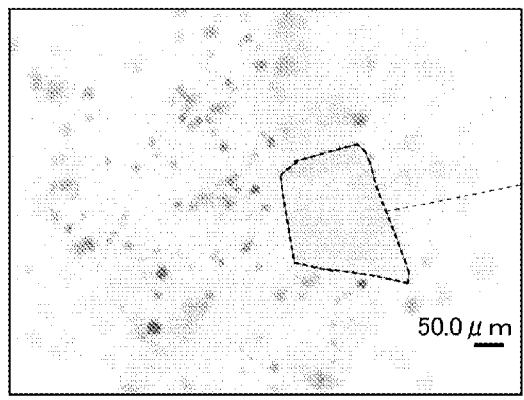

On the other hand, FIG. 4 shows GFP fluorescence microscopy images of the interior of the well of the cell sorter in which osteoclasts were not guided under the bone fragment. In this cell sorter, none of the leukemic cells got under the bone fragment even after a lapse of 4.5 hours.

From the above, it is considered that, despite the presence of the bone fragment as a barrier, the leukemic cells passed through the barrier and got under the bone fragment due to the osteoclasts present under the bone fragment. In this way, a microenvironment in which cancer cells migrate can be constructed by placing osteoclasts under the bone fragment in the well 4, and such a migration phenomenon can be observed in real time. The cells that migrated and the cells that did not migrate are different in their characteristics, and therefore, it is possible to sort out cells having the characteristic of migrating in such an environment from cells not having such a characteristic.

It is to be noted that the cell sorter and the cell sorting method according to the present invention are not limited to the above example. The cell sorter is required to satisfy the following requirements to function as a cell sorter, and its structure is not particularly limited as long as the following requirements are satisfied:
1. a microspace with a typical length of 1 mm or less in which convection does not occur in a solution;
2. low oxygen concentration close to the concentration of oxygen in a Bone-marrow microspace (at most 21% that is the same as the atmosphere, preferably 5% or lower); and
3. presence of a bone fragment and osteoclasts. It is to be noted that cytokines (TGF-β), growth factors (IGFs), $Ca^{2+}$, and chemokine discharged by bone resorption by osteoclasts are considered as substances that directly induce cell migration.

The following effects can be obtained by technologically reproducing an in vivo microenvironment using the cell sorter in such a manner as described above with reference to the example.

It is generally difficult to accurately reproduce various conditions such as oxygen concentration, nutrient concentrations, and humoral factor concentrations in every experiment using a living body. On the other hand, experimental reproducibility is improved by constructing an experimental system using a chip according to the present invention. Further, experimental conditions can be freely set, and therefore, it is also possible to freely set special conditions that cannot be achieved in a living body to observe the characteristics and behavior of cells under such conditions.

Further, an experiment using a chip can be an alternative to one using a small animal or the like, which is expected to have a significant effect also in terms of animal protection. Further, when a subject is a human, an experiment can be performed on a site, such as the brain, that is difficult to directly observe from technical and ethical point of view. Further, an experiment can be performed using not an organism but a chip that can be technically controlled, and therefore can be easily automated. The simultaneous observation of two or more chips can also be performed because the chips are easily parallelized.

Further, the capacity of the well of the chip is very small, and therefore the amounts of reagents and cells required for an experiment can be reduced, which is advantageous in terms of cost and environment. A small capacity of the well is effective also when cells or tissue that can be collected only in a small amount are/is used or a valuable and expensive reagent is used.

INDUSTRIAL APPLICABILITY

A study on a microenvironment around leukemic stem cells or sorting out of leukemic stem cells significantly contributes to the understanding of mechanism of stem cells and leads to research on the radical cure of cancer. A study on a microenvironment around the center of a tumor of solid cancer such as lung cancer or breast cancer or sorting out of tumor cells contributes to the understanding of mechanism of invasion and metastasis of cancer cells, and can be applied to research on the true nature of cancer and to suppression of metastasis. As described above, reproduction of an in vivo microenvironment in the cell sorter according to the present invention makes it possible to perform in vitro observation of the characteristics and behavior of cancer cells in an in vivo microenvironment to perform cell sorting, which has the potential to contribute not only to research on basic biology but also to treatment and drug discovery.

DESCRIPTION OF REFERENCE SIGNS

2: Chip
3a: First substrate
3b: Second substrate
4: Well
5a, 5b: Groove
6: Well bottom surface
8: Matrix
10: Bone fragment
12: Osteoclasts The invention claims is:

1. A cell sorter comprising:
  a well that has a microspace filled with a liquid and having a length of 1 mm or less and has a bottom surface made of a light-permeable material allowing optical observation of an interior of the microspace;
  a matrix provided on the bottom surface in the well;
  a bone fragment placed on the matrix in the well; and
  osteoclasts placed between the matrix and the bone fragment.

2. The cell sorter according to claim 1, wherein the matrix is a collagen gel.

3. The cell sorter according to claim 1, wherein the well has a cylindrical shape, its length is a diameter, and the well has a depth of 300 μm or less.

4. The cell sorter according to claim 1, wherein a concentration of oxygen in a position where the osteoclasts are placed is about 5%.

5. A cell sorting method comprising the steps of:
  preparing a cell sorter comprising:
    a well that has a microspace filled with a liquid and having a length of 1 mm or less and has a bottom surface made of a light-permeable material allowing optical observation of an interior of the microspace;
    a matrix provided on the bottom surface in the well;
    a bone fragment placed on the matrix in the well; and
    osteoclasts placed between the matrix and the bone fragment;
  placing sample cells labeled with a phosphor around the bone fragment in the well of the cell sorter; and
  optically observing positions of the sample cells after a lapse of a certain period of time to sort out the cells that migrate into a space between the matrix on the bottom surface of the well and the bone fragment from the cells that do not migrate.

6. The cell sorting method according to claim 5, wherein the phosphor is green fluorescent protein.

* * * * *